United States Patent [19]

Sage et al.

[11] Patent Number: 4,660,971
[45] Date of Patent: Apr. 28, 1987

[54] OPTICAL FEATURES OF FLOW CYTOMETRY APPARATUS

[75] Inventors: Burton H. Sage, Raleigh; Robert F. Adrion; Michael W. Malpass, both of Cary, all of N.C.

[73] Assignee: Becton, Dickinson and Company, Franklin Lakes, N.J.

[21] Appl. No.: 606,802

[22] Filed: May 3, 1984

[51] Int. Cl.$^4$ .................. G01N 21/05; G01N 21/64
[52] U.S. Cl. ....................................... 356/39; 356/73
[58] Field of Search ................. 356/39, 73, 317, 318, 356/335–336, 246, 38, 338; 377/10–12; 324/71.1, 71.4; 250/461.2; 350/245, 252; 73/861.41, 861.52

[56] References Cited

U.S. PATENT DOCUMENTS

| | | | |
|---|---|---|---|
| 3,351,408 | 11/1967 | Krewalk | 350/252 X |
| 3,675,768 | 7/1972 | Legorreta-Sanchez | 209/4 |
| 3,720,470 | 3/1973 | Berkhan | 356/335 |
| 3,893,766 | 7/1975 | Hogg | 356/39 X |
| 3,924,947 | 12/1975 | Hogg | 356/39 |
| 4,095,898 | 6/1978 | Fulwyler | 356/338 |
| 4,110,043 | 8/1978 | Eisert | 356/336 |
| 4,110,604 | 8/1978 | Haynes et al. | 324/71.4 |
| 4,165,484 | 8/1979 | Haynes | 324/71.4 |
| 4,240,029 | 12/1980 | Haynes | 324/71.4 |
| 4,343,551 | 8/1982 | Eisert | 356/335 |
| 4,348,107 | 9/1982 | Lief | 356/72 |
| 4,408,877 | 10/1983 | Lindmo et al. | 356/38 |
| 4,426,154 | 1/1984 | Steen | 356/317 |
| 4,541,689 | 9/1985 | Howard et al. | 350/245 X |

OTHER PUBLICATIONS

Nozzle Design for the Generation of Plane Liquid Surfaces, W. G. Eisert et al., *Cytometry*, vol. 1, No. 4, pp. 249-253 (1981).

Thomas et al, "Combined Optical and Electronic Analysis of Cells with the Amac Transducers", Journal of Histochemistry and Cytochemistry, vol. 25, No. 7, pp. 827-835, Jan. 18, 1977.

*Primary Examiner*—Vincent P. McGraw
*Attorney, Agent, or Firm*—Richard J. Rodrick

[57] ABSTRACT

A flow cytometry apparatus includes a transparent liquid flow chamber and a nozzle for providing a stream of particles, to be analyzed, through the flow chamber. A light source is provided along with a lens for focusing the light from the source at a region within the flow chamber through which the particles pass and for collecting light associated with those particles. Photoreceptors and the like are provided for detecting one or more characteristics of the particles related to light which strikes the particles. A spring or like biasing member provides and maintains stability between the lens and the flow chamber to particularly stabilize the relative axial position of the flow chamber and the lens.

12 Claims, 6 Drawing Figures

OPTICAL FEATURES OF FLOW CYTOMETRY APPARATUS

BACKGROUND OF THE INVENTION

1. Field of the Invention

The present invention relates to a flow cytometry apparatus for determining one or more characteristics of particles passing therethrough, and more particularly, concerns a flow cytometry apparatus with improved optical features.

2. Description of the Prior Art

There are a number of cell or particle analyzing devices employing flow cytometry techniques which rely on hydrodynamically focused fluid flow through a passageway for determining specific characteristics of the flowing cells or particles. Flow analysis of particles has been employed in the determination of a variety of characteristics of individual particles. This analysis is most useful in analyzing or determining characteristics of cells for the collection of information which would be useful in areas of research, hematology, immunology and the like. The researcher, for instance, may be interested in determining specific characteristics of individual cells so that such cells may be classified, identified, quantified, and perhaps sorted for further investigations or analysis.

Three instruments which rely on hydrodynamically focused fluid flow systems are sold by Becton, Dickinson and Company. One device, known as the ULTRA-FLO 100 TM Whole Blood Platelet Counter, rapidly and reliably counts whole blood platelets in the hematology laboratory. In the ULTRA-FLO 100 TM system, a trajectory of a diluted sample containing platelets passes straight through the center of the counting chamber orifice since the sample fluid is focused by a sheath of pressurized fluid. Another instrument sold by Becton, Dickinson and Company, relying on a hydrodynamically focused fluid flow system is known as the FACS TM analyzer. The FACS TM analyzer rapidly analyzes cells on the basis of fluorescence and electronic volume properties. Analysis is accomplished by introducing cells in suspension to the center of a focused liquid stream and causing the cells to pass, substantially one at a time, through the filtered and focused light from a high-power mercury-arc lamp. Each cell is individually characterized by its electronic impedance volume and by the intensity and color of fluorescence emitted while it is illuminated. Another instrument known as the FACS TM sorter utilizes fluid flow principles which are similar to the FACS TM analyzer, but further sorts the cells based on specifically detected characteristics. In all of the aforementioned systems, a sheath fluid is utilized to focus the particles or cells as they pass through the passageway associated with the analyzing or counting capabilities. Further, the FACS$^{TM}$ analyzer employs an optically clear or transparent liquid flow chamber, sometimes referred to as a flow cell, through which a stream of cells passes. Light is directed orthogonally through this flow cell to intercept the particles in a focal region thereof. Scattered light or fluorescence emitted by the particles may be detected to provide information with respect to each passing particle. U.S. Pat. Nos. 4,348,107; 4,240,029; 4,165,484 and 4,110,604 describe particle analysis sytems in which particles flowing in a stream are enveloped in a sheath fluid which focuses and confines the sample fluid (with particles) to the center of the flowing stream.

In flow cytometry apparatuses in which an incident beam of light is relied upon for obtaining information with respect to the particles, one or more lenses are normally involved in focusing the light on the particles flowing within the particle stream. Such lenses are also relied upon to collect light emitted by or scattered from the particles. One such lens assembly embodied within a particle analyzer instrument, and utilizing a transparent liquid flow chamber, is described in copending, commonly assigned patent application Ser. No. 276,738, filed in the U.S. Pat. and Trademark Office on June 24, 1981, and entitled, "Analyzer for Simultaneously Determining Volume and Light Emission Characteristics of Particles." In the invention of the aforementioned patent application, the lens assembly is positioned adjacent the outer surface of the transparent liquid flow chamber, with a thin layer of glycerol at the interface between lens assembly and flow chamber. This glycerol is an index matching medium provided to facilitate light transmission and minimize light losses. Even with this arrangement between the lens assembly and the flow chamber, a rather complicated alignment procedure is typically required to bring the particles flowing in the liquid stream through the flow chamber into the focal plane of the collection lens. For example, a three-axis adjustable lens mount is provided to establish the relative axial position of the lens assembly and flow chamber. The stability of such a lens mount is an area which needs improvement. Moreover, there is no mechanism in the presently known and used flow cytometry apparatuses to adjust the position of the flowing particle stream in order to provide the final focus with respect to the light passing through the collection lens. Of course, it is known to provide vernier adjustments for aperture sizes and microscope adjustments in flow cytometry apparatuses. For example, such vernier adjustments are described in U.S. Pat. Nos. 3,675,768 and 3,924,947.

Most present-day commercial flow cytometry apparatuses employ flow cells or chambers having cylindrical orifices and sample particle streams having a circular cross-section. Due to this geometry, significant optical aberrations, which limit the efficiency of both light collections and excitation (related to fluorescently labeled particles), are present. Moreover, these aberrations increase geometrically as the numerical aperture of the lens is increased. In general, the higher the numerical aperture, the higher the sensitivity of the flow cytometry apparatus. Aberrations thus serve to limit the practicality of using high numerical aperture lenses. In addition, as sample particle flow rate is increased, the diameter of the sample stream is increased, requiring a lens of increased depth of focus. Depth of focus is inversely proportional to the lens numerical aperture, and hence large depth of focus and high numerical aperture are mutually exclusive. It has been recognized that a large rectangular orifice within the transparent liquid flow chamber would be beneficial in optimizing the light transmission into or out of the transparent liquid flow cell. Such square orifices are described in Thomas, R.A., et al., "Combined Optical and Electronic Analysis of Cells with the AMAC Transducers," The Journal of Histochemistry and Cytochemistry, volume 25, number 7, pages 827–835, 1977, and in U.S. Pat. No. 4,348,107. It was pointed out in U.S. Pat. No. 4,348,107, however, that the optical and mechanical characteristics of a particle analyzer using a square sensing orifice enclosed inside a cube formed by adhering four pyramids together has proven to be suboptimal.

Accordingly, it is evident that improvements in the optical elements and features of flow cytometry apparatuses are still being sought which would improve the efficiency, accuracy and dependability of the light transmission characteristics related to such flow cytometry apparatuses. It is to such improvements that the present invention is directed.

SUMMARY OF THE INVENTION

A flow cytometry apparatus of the present invention includes a transparent liquid flow chamber and means for providing a stream of particles, to be analyzed, through the flow chamber. The apparatus further includes an excitation light source and lens means for focusing light from the source at a region within the flow chamber through which the particles pass. One or more characteristics of the particles, related to light which strikes the particles, are analyzed by analyzer means. Contact between the lens means and flow chamber is provided and maintained by means which stabilizes the focal region through which the particles pass.

In a preferred embodiment of the flow cytometry apparatus as described above, a transparent liquid flow chamber is included having a passageway therethrough with a rectangular cross section. The excitation light source directs light substantially orthogonally to the stream of particles. A lens is provided for focusing light from the source at a region within the passageway. This lens may also be used to collect light emitted by or scattered from the particles. A spring or like mechanism is provided for biasing the lens into contact with the flow chamber as a unitary composite structure so as to substantially eliminate relative movement therebetween and to thereby stabilize the focal region through which particles pass. A nozzle is included in the apparatus for providing a stream of particles through the passageway. This nozzle, in the preferred embodiment, has a rectangular cross section. A manually operable vernier adjustment is operatively associated with the nozzle for adjusting the position of the particles stream in the passageway to thereby optimize the focus of light on the particles within the stream.

In accordance with the principles of the present invention, a number of advantages and improvements are provided in a flow cytometry apparatus. Providing a relatively rigid connection between collection lens and flow chamber, as well as the adjustment of the particle flow stream, significantly simplifies, and renders less critical, the alignment procedure which brings the particles of the sample flow stream into the focal plane of the collection lens. As a result, these improvements not only optimize the focus of light on the particles flowing in the stream, but stabilize the focal region through which the particles pass. Since working distance tolerances of high numerical aperture objectives are on the order of ±10 microns, there is normally sufficient space in the flow chamber passageway to accomplish this adjustment by physically moving the particle stream within the passageway. Such physical movement would be accomplished by adjustment of the nozzle element which directs particles into the flow chamber. By virtue of the geometry of this motion, it may be achieved with an advantage in favor of the adjustment, i.e., a large motion of the nozzle would cause a small motion of the particle stream within the passageway. This enhances the stability and accuracy of the adjustment. Furthermore, and in the preferred embodiment hereof, a rectangular orifice or passageway, combined with a particle stream of rectangular cross section resolves the two problems articulated above related to depth of focus and aberrations affecting the use of high numerical aperture lenses. With a rectangular particle stream, the thickness of the stream can be adjusted to accommodate the reduced depth of focus of a high numerical aperture lens. The thickness of the stream, and then the flow velocity of the stream to obtain the sample volumetric flow rate, may be determined. With a large rectangular orifice or passageway, a planar, rather than cylindrical, interface exists between the lens and particle stream. The spherical aberration introduced by the planar surface is thus correctible in the lens. Since the flow chamber of the present invention is in direct contact with the lens, its position with respect to the lens surface is known, and the correction may actually be made in practice.

DETAILED DESCRIPTION

Figure 1:
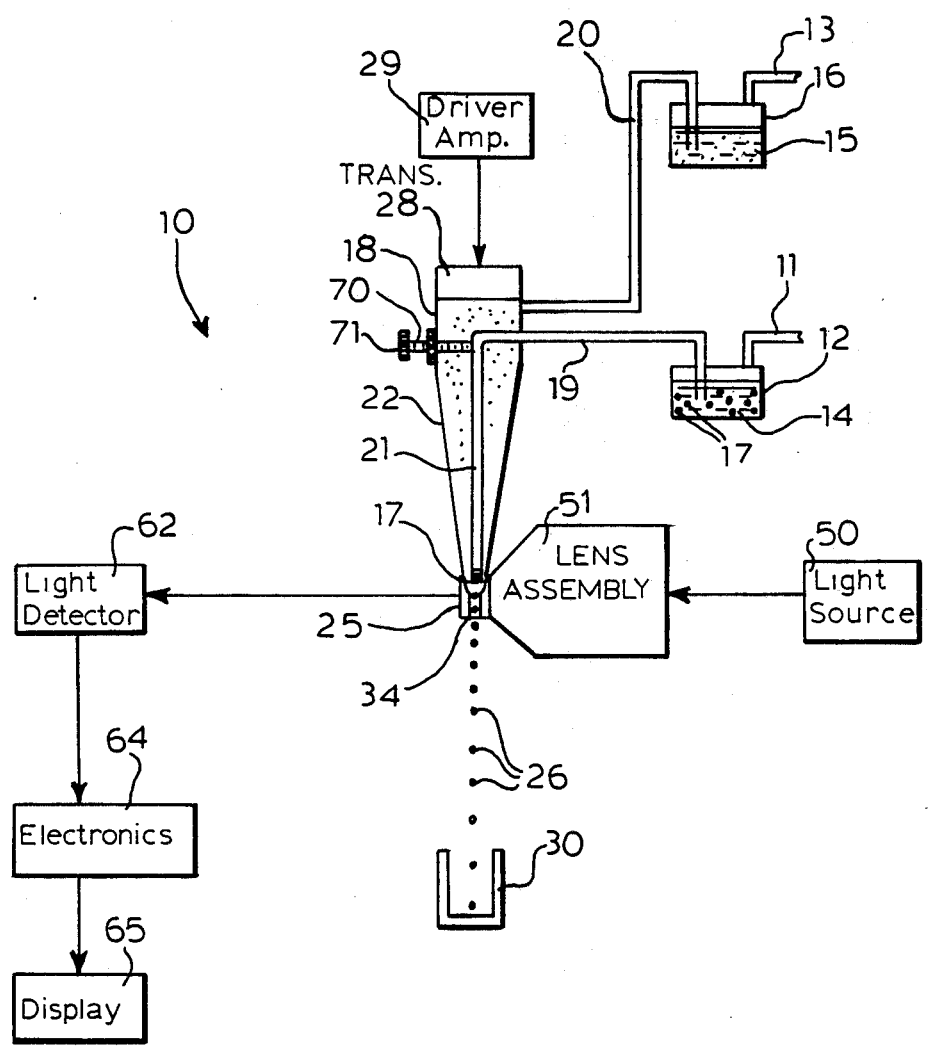
FIG. 1 is a schematic illustration of the major functional elements of the improved flow cytometry apparatus of the present invention.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings and FIG. 1 in particlar, there is illustrated a schematic representation of the preferred apparatus 10 embodying flow cytometry principles, and more specifically, utilizing a sheath fluid, in conjunction with a particle stream, in a hydrodynamically focused fluid flow system. It is understood that the present invention is useful in a variety of circumstances related to the determination of one or more characteristics of particles or cells flowing in a moving stream. Accordingly, the present invention is useful, for example, in measuring light scatter, particle volume, fluorescence or any other optical parameters for the identification, classification or quantification of particles in a sample medium.

Apparatus 10 includes a storage container 12 for holding liquid 14 containing particles 17 in suspension which are to be detected or analyzed in accordance with the present invention. A particle free sheath liquid 15 is stored in container 16. Both of the aforementioned containers may be appropriately pressurized by means of a gas pressure source or the like (not shown), through lines 11 and 13, respectively. Liquids 14 and 15 are supplied to a nozzle assembly 18 through conduits 19 and 20, respectively. Two nozzles 21 and 22 are included in nozzle assembly 18 and are supplied with liquid from containers 12 and 16, respectively, so that liquid 14 containing the particles in suspension may be jetted in a coaxial column or stream. To this end, particle containing liquid 14 from nozzle 21 is injected within nozzle 22 into the center of the flowing stream of sheath liquid 16 so that a continuous coaxial liquid flow stream results.

Nozzles 21 and 22 direct the bi-component, coaxial stream of particles 17 and sheath liquid to a transparent, preferably optically clear, liquid flow chamber 25. Flow chamber is more clearly seen in FIG. 2, taken in conjunction with FIG. 1. When the coaxial stream of particles and sheath liquid flows through flow chamber 25, the stream containing the particles is continuous. Although not necessary for the present invention, it may be desirble to form discrete droplets 26 containing particles of interest after the stream passes through flow chamber 25. To this end, droplets 26, some of which may contain particles 17, may be formed from the continuously flowing liquid stream preferably by vibration of nozzle assembly 18. To accomplish this feature, a transducer 28 and driver amplifier 29 may be provided to vibrate nozzle assembly 18 in an axial direction. Such vibration modulates the flowing liquid stream to disrupt its continuous flow and cause discrete droplets 26 to be formed. These droplets may then be collected in one or more containers 30.

Figure 2:
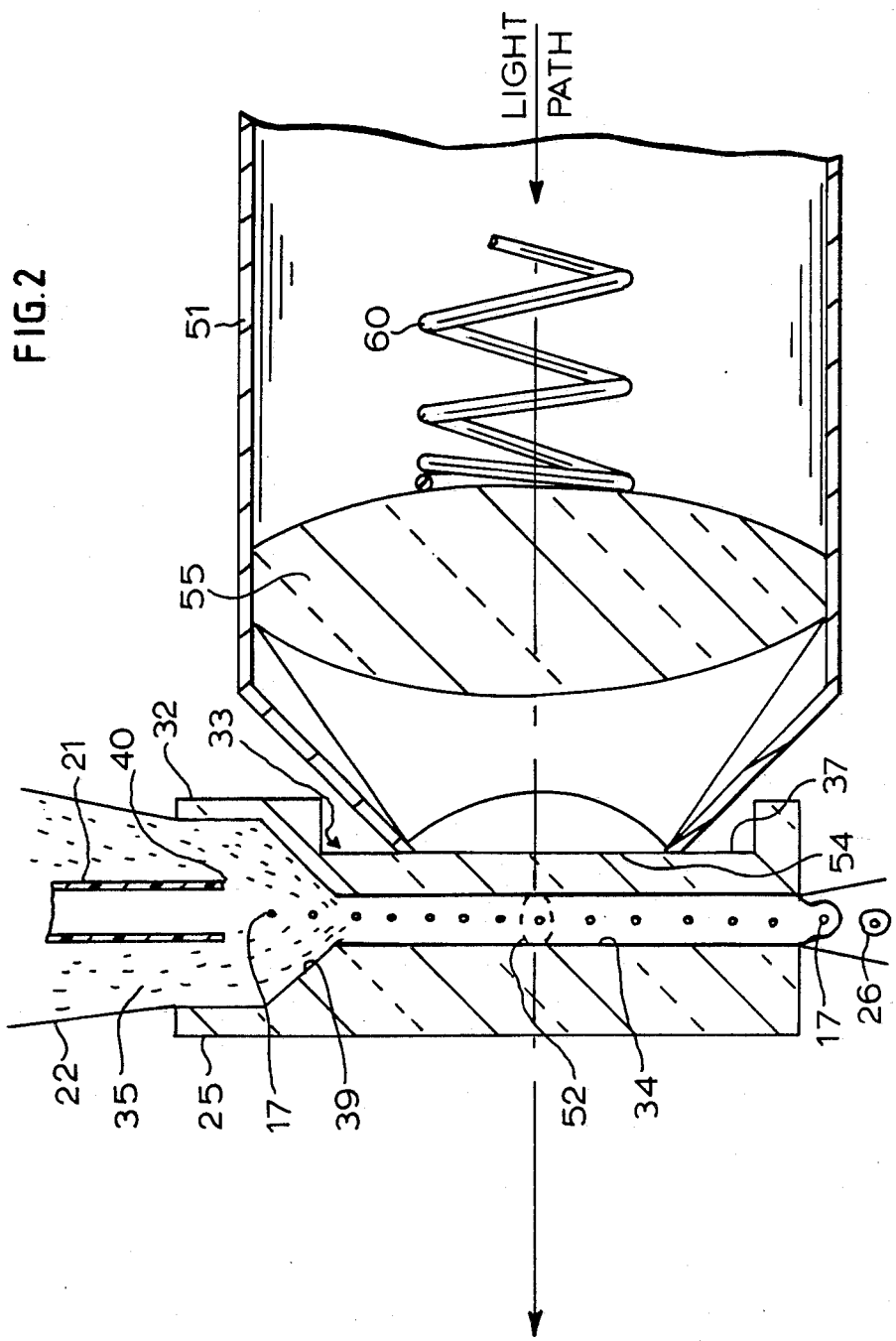
FIG. 2 is an enlarged cross-sectional view schematically illustrating the preferred arrangement of flow chamber and lens assembly of the present invention while also illustrating particle stream flow and the light path therethrough.
Figure 3:
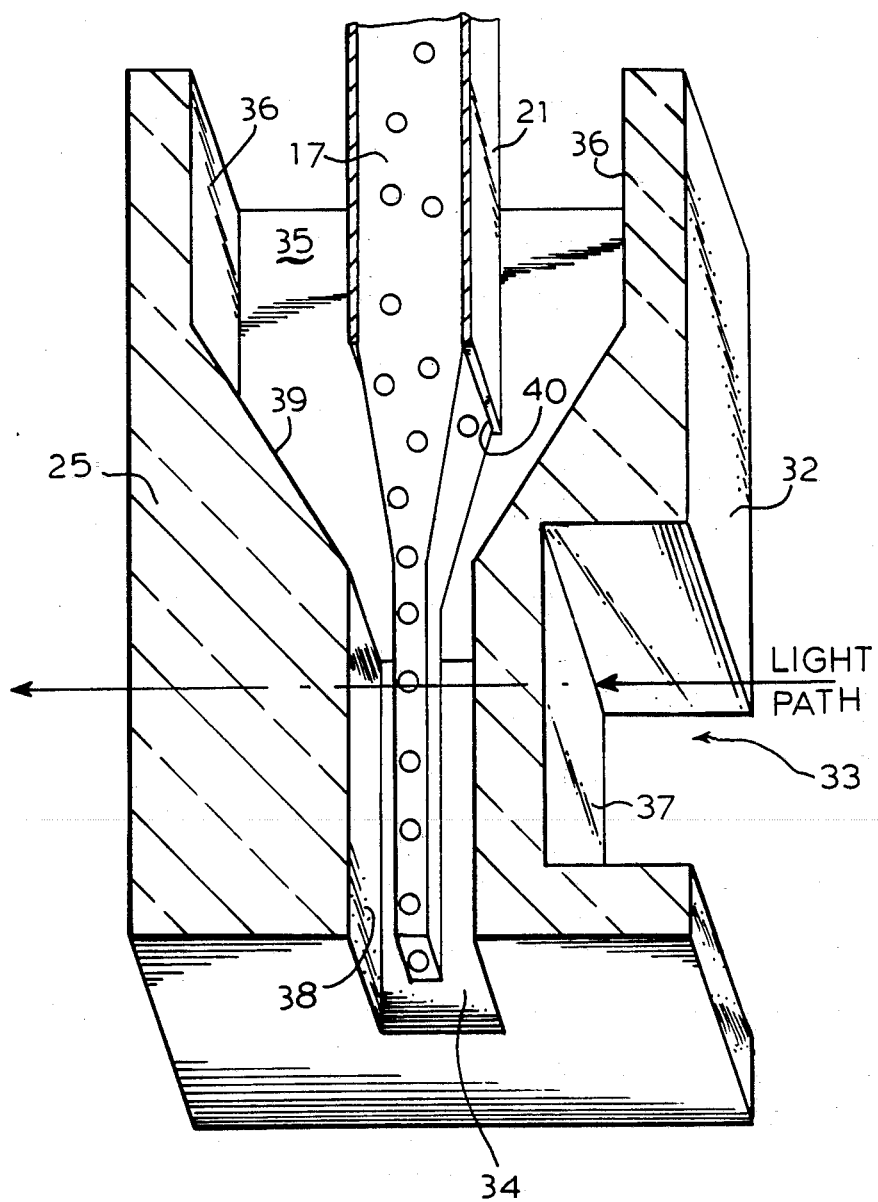
FIG. 3 is an enlarged fragmentary perspective view illustrating the preferred configuration of the nozzle and passageway through the flow chamber of the present invention.

Turning now to FIG. 3, taken in conjunction with FIG. 2, the preferred structure of liquid flow chamber 25 is illustrated. It can be seen that flow chamber 25 is a prismatic structure, and being rectangular in the embodiment being described. Other quadrilateral shapes may be employed in the flow chamber. Accordingly, flow chamber 25 includes outer surfaces 32 which are substantially flat or planar. However, a recess 33 is provided in the wall of the flow chamber so that the lens assembly can be positioned as close as possible to the particles flowing through the flow chamber. Extending through the flow chamber is a passageway 34 which may take on a variety of geometrical configurations. However, it is preferred that the cross-section of passageway 14 be rectangular or, perhaps even square, in order to achieve the desired advantages and objectives as articulated above. Accordingly, passageway 34 serves as an orifice through which the bi-component, coaxial stream containing particles 17 flows. Inasmuch as this orifice is present in the instant invention, the utilization of the well-known Coulter principle may be relied upon. According to this principle, when a nonconductive particle passes through an orifice containing an electrically conductive medium, there will be an increase in the electrical resistance at the orifice. By applying an electrical potential to the orifice, it is possible to measure the resistance increase as an electrical pulse. A proportional correlation has been established between the volume of the particle passing through the orifice and the amplitude of the electrical pulse measured as that particle traverses the orifice. In the embodiment being described, the electrodes are not shown, but the mechanism for carrying out the Coulter principle is well-known to those versed in the art.

Communicating with passageway 34 is an enlarged cavity 35 into which nozzle 21 preferably depends. Cavity 35 includes sidewalls 36 which are substantially parallel with the longitudinal walls 38 of passageway 34; a tapered transition surface 39 extends between sidewalls 36 of the cavity and sidewalls 38 of the passageway. Thus, a funnel is formed by these walls and surfaces to facilitate the flow of particles through the passageway substantially one at a time. Further, in the preferred embodiment of the present invention, nozzle 21, through which particles 17 flow, includes a distal opening 40 which is geometrically consistent with the cross section of passageway 34. Along these lines, and preferably speaking, distal opening 40 has a rectangular cross-section which also furthers the goals and objectives as mentioned above. While flow chamber 25 is fabricated so as to be transparent for the passage of light therethrough, it is preferred that the material chosen for the flow chamber provide optical clarity, as well. While there are a number of such materials which may be used, for example, different types of glass, it is preferred that the flow chamber be fabricated from fused quartz.

Optical elements, including light paths and light detection, are more clearly illustrated in FIGS. 1 and 2 to which attention is now directed. It is appreciated that the drawings herein only schematically illustrate the optical aspects of the present invention, with emphasis on the improvement hereof. For a more detailed explanation of the type of optical systems which may be employed in a typical flow cytometry apparatus, reference is made to one or more of the patents listed above. In accordance therewith, light source 50 may typically be a laser for providing coherent light at a singular wavelength, or, perhaps, may be a source of incoherent light providing light over a wider wavelength, such as a mercury or xenon-arc lamp. Light from source 50 is directed toward transparent flow chamber 25 transversely to the direction of the particle flow stream in order to intercept the particles as they pass therethrough. Preferably, light from source 50 is directed substantially orthogonally or perpendicularly to the axis representative of the stream of particles 17. A lens assembly 51 is provided in order to focus the light in a focal region 52 across passageway 34 of the transparent flow chamber, as seen in FIG. 2. Lens assembly 51 may be used to collect light emitted by or scattered from particles 17. To provide for an optimum focal region, lens assembly 51 is preferably positioned so that the leading lens face 54 is positioned directly against, and in contact with, outside surface 37 of recess 33 in the flow chamber. A very thin layer of index matching medium, such as glycerol may be applied to the interface of lens face 54 of lens 55 and flow chamber surface 37 to provide effective light transmission while eliminating any undesirable intrinsic transmission effects.

In order to assure relatively rigid connection between lens 55 and flow chamber 25, so as to form a substantially unitary composite structure to eliminate relative movement therebetewen, lens 55 is biased against flow chamber 25 by virtue of coil spring 60. The spring-loaded effect of lens against flow chamber facilitates this relatively rigid connection between these elements and contributes to the stabilization of focal region 52 through which the particles pass. The particular stabilization relates to that of the relative axial position between the flow chamber and the lens assembly. While coil spring 60 is one expedient for achieving this desirable feature, it is understood that other mechanisms devisable by those skilled in the art fall within the purview of the present invention. Whatever the specific mechanism, as long as relative movement between the lens and flow chamber is eliminated or substantially reduced, the opportunity to provide a well-defined focal region is increased in accordance with the present invention.

Light scattered, emitted or otherwise associated with the particles passing through the illuminated focal region of the flow chamber is then detected by light detector 62. This light detector may be a well-known photomultiplier device which converts light signals to electrical pulses so that information with respect to the detected light may be electrically analyzed. If light source 50 is an arc lamp, in actual practice light detector 62 would typically be located on the same side of the lens assembly as the light source. For example, an epi-illumination configuration could be employed. On the other hand, if light source 50 is a laser, a low numerical aperture lens may be included between the flow chamber and the light detector, in the configuration illustrated in FIG. 1. Although light detector 62 is illustrated in FIG. 1 as being in-line with light from source 50, this configuration is typical in flow cytometry apparatuses when detecting scattered light. To detect fluorescence, light detector 62 is typically oriented at right angles to the path of incident light.

An electrical pulse associated with detected light may be fed to the electronics 64 of the flow cytometry apparatus whereupon information relating thereto may be seen on a display 65, stored in a computer (not shown) or fed back into the apparatus for further analysis.

Figure 4:
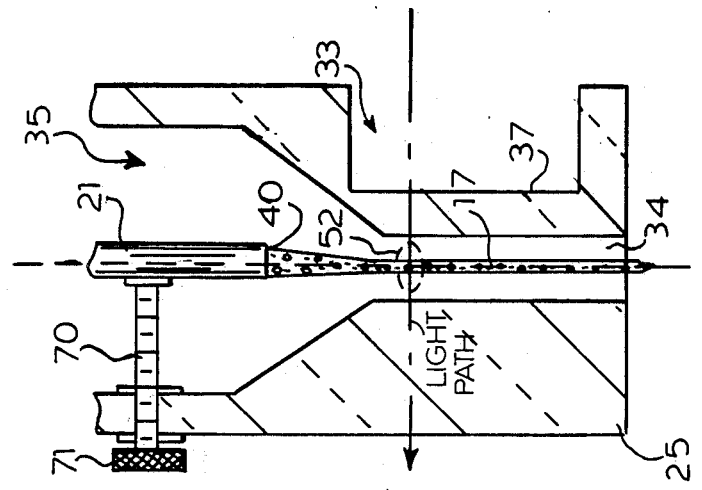
FIGS. 4–6 are cross-sectional views of the preferred flow chamber of the present invention illustrating the adjustable positioning of particle stream flow therethrough.
Figure 5:
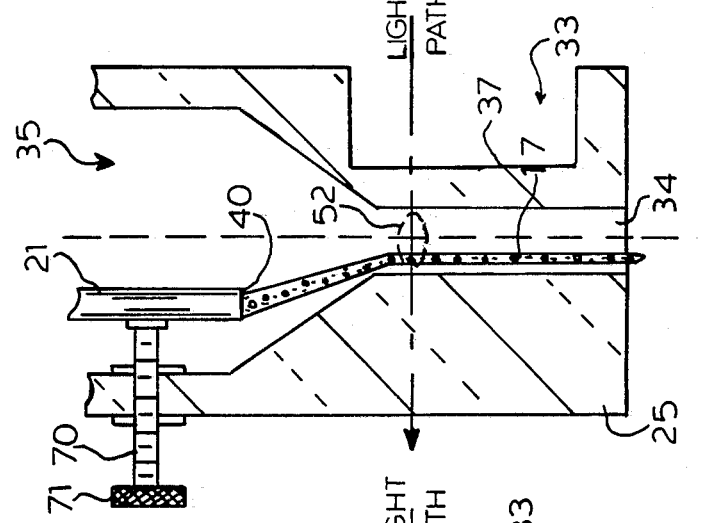
Figure 6:
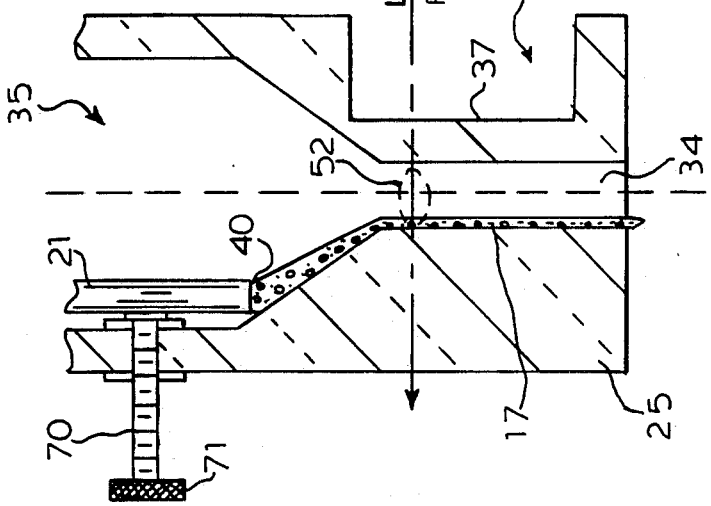

Taking into account the fixed connection between the lens and flow chamber, focusing the light in the focal region of the flow chamber, through which particles pass, is accomplished by adjusting the position of nozzle 21. Such adjustment feature is illustrated in FIGS. 4–6. For example, in FIG. 4, nozzle 21 is illustrated as being aligned substantially along the longitudinal axis of passageway 34. In the event that the optimal intensity in focal region 52 is somewhat offset from the longitudinal axis of passageway 34, nozzle 21 may be adjusted, as seen in FIGS. 5 and 6. Although all the details of the mounting structure of the nozzle are not illustrated, FIGS. 5 and 6 demonstrate schematically that a rotatable shaft 70 is connected to nozzle 21. By utilizing screwthreads or the like, turning of thumbwheel or knob 71 causes a lateral translation of nozzle 21, in either direction with respect to the longitudinal axis of passageway 34. In this fashion, distal opening 40, through which particles 17 exit, is physically moved to cause the position of the particle stream to become offset from the longitudinal axis of the passageay as the particle stream flows therethrough. Keeping in mind that the particle stream is still ensheathed by sheath fluid as it flows through the passageway, a relatively large lateral movement of nozzle 21 causes a relatively small movement of the particle steam in the passageway. Thus, the manually operable vernier adjustment provided by shaft 70 and thumbwheel 71 not only allows the fine tuning for focusing purposes, but enhances the stability and accuracy of the adjustment. It is also within the scope of the present invention to fabricate a unitary structure embodying flow chamber 25 and the last lens element 55 of the lens assembly from the same transparent material so as to assure the position of the desired focal region within the passageay of the flow chamber.

While the embodiment being described herein provides for the lateral adjustment of the flow nozzle with respect to the fixed position of the flow chamber, it is also within the purview of the present invention to optimize the intensity of the focal region by other mechanisms. For instance, and not limted thereto, nozzle 21 may be mounted within the flow cytometry apparatus so as to be in a fixed position. Focus of the light within passageway 34 is optimized by a vernier adjustment, similar to that described in conjunction with FIGS. 4–6, associated with lateral movement of flow chamber 25. Other schemes for achieving this desirable focus will be evident to those versed in the art.

Thus, the present invention provides improved optical features of a flow cytometry apparatus which relies upon light energy as the mechanism for deriving information of certain characteristics of moving particles, cells or the like. The features of the present invention improve the stability and accuracy of the adjustment for focusing light on the particles, while also eliminating or minimizing optical aberrations by virtue of the geometry of the passageway through which particles flow and the nozzle or the like device from which the particle stream is introduced into the flow chamber. In particular the flow chamber-lens contact and the lens-cell transverse adjustment mechanisms described above together define and stabilize the three-dimensional relative position of the flow chamber and the lens.

What is claimed:

1. In a flow cytometry apparatus of the type including a transparent liquid flow chamber with a passageway therethrough, means for providing a stream of particles to be analyzed through the passageway of said flow chamber, an excitation light source, lens means for focusing light from said source at a region within the passageway of said flow chamber through which said particles pass and for collecting light associated with said particles, and means for determining one or more characteristics of said particles related to said light which strikes said particles, wherein the improvement comprises:

means for providing and maintaining relative stability between said lens means and said flow chamber to stabilize the relative axial position of said flow chamber and said lens means, said lens means being in contact with said flow chamber; and means for focusing the light in order to optimize its intensity in said focal region, said focusing means further including means for adjusting the relative position of the stream of particles with respect to the flow chamber.

2. The improved apparatus of claim 1 wherein said means for providing and maintaining includes a spring which biases said lens means in contact with said flow chamber.

3. The improved apparatus of claim 1 wherein said means for providing and maintaining further includes a thin layer of index matching medium at the interface of said lens means and said flow chamber to facilitate light transmission.

4. The improved apparatus of claim 1 wherein said means for providing and maintaining further joins said lens means and said flow chamber as a unitary, composite structure so as to substantially eliminate relative movement between said lens means and said flow chamber.

5. The improved apparatus of claim 1 wherein said lens means and said flow chamber are integrally formed from the same material.

6. The improved apparatus of claim 1 wherein said adjusting means includes a manually operable vernier adjustment to fine tune the position of said particle stream as said stream of particles passes through the focal region to thereby optimize the focus of said light on said particles.

7. The improved apparatus of claim 1 wherein said adjusting means includes a manually operable vernier adjustment to fine tune the position of said 8. The improved apparatus of claim 1 wherein said passageway has at least a portion thereof which is rectangular in cross-section.

9. The improved apparatus of claim 8 wherein said means for providing the stream of particles includes a nozzle.

10. The improved apparatus of claim 9 wherein said nozzle has a rectangular cross-section.

11. The improved apparatus of claim 1 wherein said flow chamber is made of fused quartz.

12. In a flow cytometry apparatus of the type including a transparent liquid flow chamber with a passageway therethrough having a rectangular cross-section, means for providing a stream of particles to be analyzed through said passageway, an excitation light source for directing light substantially orthogonally to said stream of particles, a lens for focusing light from said source at a region within said passageway and for collecting light associated with said particles, and means for determining one or more characteristics of said particles related to said light which strikes said particles, wherein the improvement comprises:

a spring for biasing said lens into contact with said flow chamber as a unitary, composite structure so as to subtantially eliminate relative movement therebetween and to thereby stabilize the relative axial position of said flow chamber and said lens;

said means for providing including a nozzle having a rectangular cross-section; and a manually operable vernier adjustment operatively associated with said nozzle for adjusting the position of said particle stream in said passageway to thereby optimize the focus of said light on said particles within said stream.

* * * * *

UNITED STATES PATENT AND TRADEMARK OFFICE
CERTIFICATE OF CORRECTION

PATENT NO. : 4,660,971

DATED : April 28, 1987

INVENTOR(S) : Sage et al.

It is certified that error appears in the above-identified patent and that said Letters Patent are hereby corrected as shown below:

Column 9, line 12:
(Claim 7)

after "said" insert --particle stream as said stream of particles passes through the focal region to thereby optimize the focus of said light on said particles--.

Signed and Sealed this

Third Day of November, 1987

Attest:

DONALD J. QUIGG

Attesting Officer      Commissioner of Patents and Trademarks